(12) United States Patent
Jurna et al.

(10) Patent No.: US 10,849,784 B2
(45) Date of Patent: Dec. 1, 2020

(54) RADIO-FREQUENCY SYSTEM FOR SKIN TREATMENT INCLUDING A ROLLER WITH AN ELECTRODE AND A METHOD FOR SKIN TREATMENT

(71) Applicant: KONINKLIJKE PHILIPS N.V., Eindhoven (NL)

(72) Inventors: Martin Jurna, Eindhoven (NL); Jonathan Alambra Palero, Eindhoven (NL); Margaret Horton, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1078 days.

(21) Appl. No.: 14/399,055

(22) PCT Filed: May 1, 2013

(86) PCT No.: PCT/IB2013/053439
§ 371 (c)(1),
(2) Date: Nov. 5, 2014

(87) PCT Pub. No.: WO2013/168051
PCT Pub. Date: Nov. 14, 2013

(65) Prior Publication Data
US 2015/0142087 A1 May 21, 2015

Related U.S. Application Data

(60) Provisional application No. 61/643,388, filed on May 7, 2012.

(51) Int. Cl.
*A61F 7/00* (2006.01)
*A61N 1/32* (2006.01)

(52) U.S. Cl.
CPC .............. *A61F 7/007* (2013.01); *A61N 1/328* (2013.01); *A61F 2007/0052* (2013.01); *A61F 2007/0087* (2013.01)

(58) Field of Classification Search
CPC ...... A61F 2007/0052; A61F 2007/0087; A61F 7/007; A61N 1/328
See application file for complete search history.

(56) References Cited

U.S. PATENT DOCUMENTS 4,175,551 A  11/1979  D'Haenens
5,919,219 A  6/1999  Knowlton
(Continued)

FOREIGN PATENT DOCUMENTS

JP  2001289562 A  11/2007
JP  2007289562 A * 11/2007
(Continued)

OTHER PUBLICATIONS

English translation of Moriguchi, Yoshiyuki, Nov. 8, 2007, Application No. JP2006123296 (Year: 2007).*
(Continued)

*Primary Examiner* — Linda C Dvorak
*Assistant Examiner* — Tigist S Demie

(57) ABSTRACT

A method of treating a skin tissue relief feature (3) in mammalian, in particular human, skin tissue (1) is provided. The method comprises the steps of: determining a perimeter (4) of the relief feature and inducing contraction of skin tissue areas (5) present on opposite sides of the relief feature in positions adjacent to respective portions of the perimeter in a direction of contraction substantially parallel to a skin surface and substantially normal to the respective portions of the perimeter. A system is also provided comprising a radio-frequency source (9) and an applicator with a roller.

15 Claims, 5 Drawing Sheets

(56) References Cited

U.S. PATENT DOCUMENTS

| | | |
|---|---|---|
| 6,852,110 B2 | 2/2005 | Roy |
| 2004/0073079 A1* | 4/2004 | Altshuler ............. A61B 5/6843 600/1 |
| 2004/0230227 A1 | 11/2004 | Avrahami |
| 2006/0047281 A1 | 3/2006 | Kreindel |
| 2006/0173518 A1 | 8/2006 | Kreindel |
| 2007/0073121 A1 | 3/2007 | Hoarau |
| 2007/0232966 A1 | 10/2007 | Applebaum |
| 2008/0183167 A1* | 7/2008 | Britva .................. A61B 18/042 606/41 |
| 2009/0299361 A1* | 12/2009 | Flyash .................. A61B 18/14 606/33 |
| 2010/0210993 A1 | 8/2010 | Flyash |
| 2010/0274238 A1* | 10/2010 | Klimovitch ........ A61B 18/1442 606/33 |
| 2011/0015625 A1 | 1/2011 | Adanny |
| 2011/0245735 A1 | 10/2011 | Eckhouse |

FOREIGN PATENT DOCUMENTS

| | | |
|---|---|---|
| JP | 2011512227 A | 4/2011 |
| RU | 2008125044 A | 12/2009 |
| WO | 2008091983 A2 | 7/2008 |
| WO | 2010097790 A1 | 9/2010 |
| WO | 2012023129 A1 | 2/2012 |

OTHER PUBLICATIONS

Malcolm Paul, Three Dimensional Radiofrequency Tissue Tightening: A Proposed Mechanism and Applications for Body Contouring. Aesth Plast Surg (2011) 35:87-95.

* cited by examiner

RADIO-FREQUENCY SYSTEM FOR SKIN TREATMENT INCLUDING A ROLLER WITH AN ELECTRODE AND A METHOD FOR SKIN TREATMENT

This application is the U.S. National Phase application under 35 U.S.C. § 371 of International Application No. PCT/IB2013/053439, filed on May 1, 2013, which claims the benefit of U.S. Provisional Application No. 61/643,388 filed on May 7, 2012. These applications are hereby incorporated by reference herein.

TECHNICAL FIELD

The present disclosure relates to skin treatment, in particular radio-frequency treatment of mammalian skin tissue, more in particular human skin and subdermal tissue. The treatment is primarily suitable for skin tightening and/or skin rejuvenation.

BACKGROUND

Various techniques are known for tightening skin, treating wrinkles and/or providing skin rejuvenation. In particular creation of small skin lesions which provoke a natural regeneration reaction of the skin tissue has proven a successful technique. The lesions may be thermally inflicted, based on thermolysis by heating the dermal tissue. Dermal collagen contracts when it is heated at temperatures approximately between 60° C. and 70° C., and it denatures at higher temperatures. The tissue contraction and shrinkage can reach tens of percents of the heated tissue volume, and results in tightening of the skin and reduction of wrinkles, fine lines and skin laxity. Furthermore, it also rejuvenates the skin by stimulating the synthesis of new collagen. Application of electromagnetic energy at radio frequencies (RF energy) to heat the skin tissue has proven to be very effective.

However, for accurate treatment, proper positioning of the RF electrodes on the skin and dosing of the energy are required to prevent under- or overheating. E.g. US 2010/210993 discloses an apparatus for personal skin treatment which includes an RF generator and an applicator with at least a pair of electrodes mounted on the distal end of the applicator. The electrodes are configured for applying an RF voltage to a subject skin. The RF voltage generator supplies the electrodes with the RF voltage. The applicator may include a feedback system for controlling proper treatment.

Such apparatus is complex and may provide unsuccessful and/or uncontrolled treatment due to varying contacts between the radio-frequency contacts and the skin to be treated upon moving the apparatus. Also, if contact between the radio-frequency contacts and the skin is lost, discharges may occur which are generally perceived as painful and which should be avoided.

Further, at present a method or device for treatment of single skin relief features, in particular elongated features such as fine lines or wrinkles is still lacking.

An improved method and system are therefore desired.

SUMMARY

Herewith, a method of treating a skin tissue relief feature in mammalian, in particular human, skin tissue is provided. The method comprises the steps of: determining a perimeter of the relief feature and a number of skin tissue areas present on opposite sides of the relief feature in positions adjacent to respective portions of the perimeter at an outward side of the perimeter, and inducing contraction of the skin tissue areas in a direction of contraction substantially parallel to a skin surface and substantially normal to the respective sections of the perimeter.

Thus, the contracted skin tissue areas exert a pulling force on the skin tissue relief feature to flatten the relief feature and reduce the skin relief so that a more even appearance is achieved. In case of a rounded feature, e.g. a dimple or a bulge, the direction of contraction may be generally radial to the relief feature.

Contraction of collagen of a portion of the skin tissue area may in particular be induced reliably by heating the portion of the skin tissue area to a temperature in a range of 60-70 degrees Celsius, which may be controlled by monitoring the skin tissue temperature, possibly using a feedback system to maintain the portion of the skin temperature at such desired temperature for a desired period of time. Inducing contraction in such a manner is reliable and predictable, and may be noninvasive and may not require healing. Hence, the method is user friendly.

The skin relief feature may be an elongated feature having a direction of elongation, such as a fine line or wrinkle. Then, the skin tissue areas may extend along the elongated feature and substantially parallel to the direction of elongation. Thus, e.g. with the skin relief feature being a wrinkle, the relief of the feature may be effectively reduced and possibly the relief feature may be removed substantially completely.

In an effective embodiment of the method, the step of inducing contraction comprises applying radio-frequency energy to a portion of the skin tissue areas via at least one radio-frequency electrode. Application of radio-frequency is a proven technology, the effects of which can be accurately modeled and controlled. This facilitates providing the skin tissue contraction and according skin relief reduction as intended, preventing accidental over- or under-treatment. In particular bipolar radio-frequency application facilitates determining a direction of the radio-frequency field, which may be primarily directed in the desired direction of contraction.

When using radio-frequency, the step of inducing contraction may comprise causing (mechanical) contact between the radio-frequency electrode and the skin-surface in a plurality of, possibly successive, contact areas of the skin surface, and applying the radio-frequency energy with the radio-frequency electrode in contact with the skin surface. This facilitates use of relatively small contact areas with respect to the skin tissue areas to be treated and it allows use of relatively small electrodes that facilitate accurate application and/or dosing of the radio-frequency energy. Use of plural contact areas along the skin tissue relief feature, e.g. by displacing one or more radio-frequency electrodes, enables tracing the perimeter or contour of the feature and/or adaptation of the direction of contraction to suit the feature's shape and possible anatomic details. Providing different contact areas along the skin, in particular with the electrode(s) in contact with the skin surface, allows treating significant areas of skin tissue and providing a smooth and even effect.

Plural contact areas may be adjacent to each other and contact each other and/or they may overlap each other at least partly, e.g. to ensure that no portion of a skin tissue area is skipped and/or to provide a gradually varying treatment intensity.

By using a roller comprising the radio-frequency electrode, and by rolling the roller over the skin surface and causing contact between the radio-frequency electrode and the skin surface in a plurality of successive contact areas of the skin tissue areas, causing contact between the radio-frequency electrode and the skin-surface in a plurality of successive contact areas of the skin surface may be achieved. Thus the locations where the radio-frequency is applied via the contact area may be distributed over the skin by rolling the radio-frequency electrode over the skin. This facilitates maintaining contact between the electrode(s) and the skin so as to prevent RF discharges which may damage the skin, e.g. by ablation of skin tissue, which is perceived as uncomfortable, may have side effects and require healing, but which otherwise may have no negative effect on the treatment and in fact may be beneficial to the skin. Also, it facilitates tracing a particular desired trajectory and/or reduces the risk of unwanted skin tissue deformation by dragging skin along with the electrode(s) and possible associated accidental misalignment of the direction of contraction.

Although contraction may be induced along substantially the entire perimeter of the feature, it is possible to treat a series of smaller skin tissue areas adjacent the feature to achieve the desired effect at less energy use, treatment duration and/or exposure of the skin tissue to the treatment, thus reducing (risk of) erythema or overtreatment. It is however considered beneficial if the treated skin tissue areas extend along a section of the perimeter with a spatial distribution duty cycle of treated skin tissue relative to untreated skin tissue of about 50% or more, so that the treated skin tissue areas are distributed along the perimeter but exceed the untreated areas in size.

In an embodiment, contraction of at least two skin tissue areas present on opposite sides of the skin tissue relief feature is induced substantially simultaneously. This may reduce duration of a particular treatment and it facilitates achieving a symmetric effect.

Contraction of skin tissue areas present on opposite sides of the relief feature may be achieved substantially simultaneously in an efficient manner by displacing the electrodes on opposite sides of and parallel to the skin tissue relief feature.

In an embodiment, the elongated feature is a wrinkle, and the contraction of the skin tissue areas present on opposite sides of the wrinkle is induced substantially simultaneously by using a roller comprising at least two radio-frequency electrodes, and by rolling the roller over the skin surface in a direction parallel to the wrinkle, wherein the two radio-frequency electrodes are in contact with the skin surface on respective opposite sides of the wrinkle to apply radio-frequency energy to the skin tissue areas.

Also, a method is provided of treating mammalian, in particular human, skin tissue with electromagnetic energy. The method comprises applying radio-frequency energy to a portion of the skin tissue by contacting the skin at a contact area with a radio-frequency electrode and displacing the contact area substantially continuously over the skin by rolling the radio-frequency electrode over the skin and in contact with the skin. Thus, larger areas of skin tissue than the contact area are treated with little to no risk of damage of skin tissue from discharges such as burning and/or ablation.

An embodiment comprises applying radio-frequency energy to a portion of the skin tissue by contacting the skin at two contact areas with radio-frequency electrodes wherein the electrodes are interconnected and operated for bipolar radio-frequency signal generation, and wherein the method further comprises displacing the contact areas substantially continuously over the skin by rolling the radio-frequency electrodes over the skin and in contact with the skin. This facilitates application of radio-frequency energy in a well-defined area.

An embodiment comprises treating an elongated skin portion, comprising applying radio-frequency energy to a portion of the skin tissue by contacting the skin at two contact areas with radio-frequency electrodes, wherein the contact areas are arranged on opposite sides of the elongated skin portion and wherein the method further comprises displacing the contact areas substantially continuously over the skin by rolling the radio-frequency electrodes over the skin and in contact with the skin. Displacing the contact areas along the elongated skin portion, e.g. along a tension line in the skin of a mammalian e.g. human subject, improves effectiveness of the treatment, in particular when arranging the contact areas on opposite sides of one dimensional skin features.

An embodiment comprises applying the radio-frequency dependent on the displacement speed of the contact area. This facilitates preventing overtreatment or undertreatment. The displacement speed may be determined by measuring one or more aspects from the treated skin tissue and/or from movement of at least one part of the electrode, e.g. a rolling speed.

Further, a system for treating skin tissue with electromagnetic energy according to the appended claims is provided. The system comprises a radio-frequency source and an applicator. The applicator comprises a manipulator and a roller which is rotatable about an axis of rotation and comprises at least one radio-frequency electrode for contacting a skin surface at successive contact areas of the skin surface. The radio-frequency electrode is couplable or coupled with the radio-frequency source, and the roller is rotatable and configured for, in use, causing the radio-frequency electrode to contact the successive contact areas of the skin surface by rotation of the roller over the skin surface. The system is configured to apply the radio-frequency energy to the skin tissue only via direct mechanical contact between the radio-frequency electrode and the skin surface when the roller is in direct mechanical contact with the skin surface.

Thus, the contact area, and consequently the treatment area, may be varied by rolling the roller over the skin which enables control of the position, contact and/or contact force between the electrode and the skin during the displacement. Also, (arcing) discharges between the RF electrode and the skin are prevented by the rolling construction, which discharges could occur when (at least direct electrical) contact between the electrode and the skin is lost, e.g. due to stick-slip motion of a non-rotational electrode over the skin. Such discharges may damage the skin e.g. by ablation of skin tissue which is perceived as uncomfortable, may have side effects and require healing. Prevention of discharges may furthermore be achieved if the system is provided with a controller and a sensor for detecting contact between the skin and the electrode(s), e.g. by detecting electrical impedance variations in a circuit connected to the electrode upon contact with the skin. Suitable systems are known in the art. A curved electrode suitable for rolling may also assist in flattening the skin by pressure and/or improving contact by following the anatomic contour of the body portion of which the skin is to be treated.

The roller and the radio-frequency electrode may be configured for, in use, causing the radio-frequency electrode to contact the skin surface continuously by rotation of the radio-frequency electrode in contact with the skin surface.

This facilitates providing a continuous skin surface area to which the RF energy is applied and facilitates prevention of discharges.

Generally disc- or wheel shaped rollers may be provided for rotation about a predetermined axis of rotation. In an embodiment, the roller is generally ball-shaped facilitating rolling in any direction.

In an applicator comprising plural electrodes, one or more electrodes may be operated individually.

In an embodiment, the roller is rotatable about the axis of rotation over a first angular range, and the radio-frequency electrode has a contact surface for contacting the skin surface which extends continuously about the axis of rotation over a second angular range equal to or larger than the first angular range, e.g. being elongated in the circumferential direction. This allows continuous displacement of the contact area over the full rotational freedom of the roller and prevents loss of contact between the electrode and the skin surface by rolling the roller further than the length of the electrode in the direction of rotation. E.g., if the electrode extends circumferentially over the roller over an angular range of about 180 degrees about the axis of rotation, continuous contact between the electrode and the skin surface over a distance of about equal to the diameter of the roller is facilitated if the roller can roll that far.

In a particular embodiment, the roller is rotatable about an axis of rotation and the electrode has a contact surface for contacting the skin extending 360 degrees about the axis of rotation, e.g. extending substantially annularly about the axis of rotation. Thus, the electrode may be displaced substantially continuously over a distance longer than the circumference of the roller and the angular position of the roller with respect to the skin is irrelevant for establishing contact between the skin surface and the electrode. The electrode may advantageously be configured to contact the skin surface at a substantially constant position relative to the roller's position and in particular its axis of rotation, e.g. by providing an electrode extending substantially radially at one axial position. This facilitates determination and control of the contact area. In an embodiment with a cylindrical roller, the axis of rotation may be fixed. In an embodiment with a ball-shaped roller, the axis of rotation may be fixed, fixable or arbitrarily variable. In particular in case of the latter embodiment, the roller may comprise a continuous electrical conductive surface, e.g. the roller being a massive or hollow, preferably generally spherical, body of an electrically conductive material such as a metal and/or a conducting plastic or an insulating body with an electrically conductive coating.

In an embodiment, the system comprises at least two radio-frequency electrodes for contacting the skin concurrently at respective contact areas, and is couplable or coupled with the radio-frequency source for applying radio-frequency energy to the skin tissue, each electrode being rotatable with about a respective axis of rotation such that the electrodes are rotatable and configured for, in use, causing the electrodes to contact successive respective contact areas of the skin surface by rotation over the skin surface. Thus, treatment of skin tissue over a relatively large area is facilitated.

The electrodes may be arranged in an array or in any desired geometry. In a preferred embodiment, the system comprises at least two radio-frequency electrodes arranged at a mutual distance in an axial direction of the axis of rotation for contacting the skin surface concurrently at respective contact areas, each radio-frequency electrode being couplable or coupled with the radio-frequency source for applying radio-frequency energy to the skin tissue, and each radio-frequency electrode being rotatable about the axis of rotation. Thus, two or more contact areas are arranged at a mutual distance along the axis of rotation.

The electrodes may be individually rotatable, e.g. the applicator comprising plural rollers having one or more electrodes. This facilitates displacing the applicator about the skin in a curved pattern, since turning of the applicator entails different radii of curvature for the inner and outer curves to be traced by the different electrodes. Stick-slip motion of the electrodes with respect to the skin surface with possible moments of poor contact and/or arcing discharges due to sideways movement of the electrode(s) may be reduced or even prevented, allowing continuous displacement.

Individual freely rotatable ball-shaped rollers may behave even better than individual electrodes on a common axis of rotation. However, simplicity and/or robustness of the applicator may improve when the applicator comprises a roller having an insulating body provided with plural rollers, e.g. circumferential electrodes which are arranged axially offset at a mutual distance in an axial direction, in particular when the applicator comprises a single such roller rather than plural separate rollers. Note that in an embodiment with plural rollers one or more rollers may be individually suspended; this may facilitate accommodating height level differences in the treated body portion. A similar effect may be achieved by arranging plural rollers on a flexible axle.

The electrodes may be configured for rolling about the same axis of rotation, in particular with the electrodes extending substantially parallel each other with respect to the axis of rotation and wherein the electrodes may have about equal diameter/about equal circumferential size and shape. This provides a row of contact areas in a direction along the axis of rotation, which may be substantially parallel to the axis of rotation. Providing such row may be most easily realized by providing an insulating roller with plural electrode paths extending parallel each other on the surface of the roller. The roller may have a cylindrical portion and/or have doubly-curved surface portion having a varying diameter with respect to its axis of rotation, e.g. having a barrel- or ball-shaped portion. The latter options may be particularly useful for treating generally hollow body portions such as in the neck, the elbow pits, etc.

In an embodiment, plural electrodes are rotatable about a common axis of rotation and are couplable or coupled with the radio-frequency source for bipolar operation. Thus, providing plural treatment areas adjacent each other is facilitated. This facilitates treating large areas of skin tissue. By operating neighboring electrodes in bipolar arrangement, the radio-frequency field extends between the electrodes and its direction may therefore be accurately known. Plural electrodes may be arranged in a row or in an array to facilitate orienting the direction of treatment and/or treating a relatively large tissue area. Plural generally annular electrodes may be arranged axially offset with respect to the common axis of rotation to align the direction of the radio-frequency field parallel to the axial direction.

A particular embodiment comprises at least two pairs of bipolar radio-frequency electrodes wherein the pairs are arranged at a mutual distance in the axial direction and rotatable about the axis of rotation and couplable or coupled with the radio-frequency source for bipolar operation. This facilitates treating a skin relief feature concurrently on opposite sides with bipolar RF treatment.

Elongated skin features such as wrinkles and fine lines, also sometimes referred to as "one dimensional skin features", generally comprise structurally oriented features of the skin created in the direction of the tension lines within the human body. The basic pattern of the skin tension lines in the human body can be known from anatomic publications. E.g. see: http://www.tpub.com/content/armymedical/MD0574/-MD05740043.htm. By directing the radio-frequency field and thus the contraction of the collagen perpendicular to the orientation of the tension line, the one dimensional feature can be treated more effectively. Having the electrodes axially offset with respect to the common axis of rotation ensures that the field extends substantially axially with respect to the axis of rotation. This facilitates orienting the direction of treatment. Note that the electrodes may have a differently shaped contact surface, e.g. undulating or zig-zagging, so that controlled variations of the axial separation and/or the actual direction of the field about the general direction of the treatment may be provided.

An embodiment comprises a controller for controlling operation of the radio-frequency source. Thus, operation of the system is further facilitated. The controller may be configured to control operation of the RF source with respect to the emitted power from one or more electrodes, the radio-frequency, continuous, pulsed and/or otherwise modulated operation. The controller may comprise a memory and be programmable.

An embodiment comprises at least one sensor configured to provide a signal indicative of at least one of contact between the radio-frequency electrode and the skin tissue, radio-frequency power deposition into the skin tissue, treatment effectiveness and roller movement with respect to at least one of an applicator portion and the skin surface. Thus, feedback and/or control over operation of the system and/or treatment effectiveness is facilitated. The sensor may comprise a thermal sensor, an electrical sensor, a mechanical and/or an optical sensor. Plural sensors may be provided. A thermal sensor may be coupled to the electrode and or to the skin of the treated subject, and it may be of any type including an optical sensor detecting thermal radiation. An electrical sensor may be configured to monitor at least a portion of a radio-frequency signal supplied to the electrode and/or a portion of a radio-frequency signal reflected from the electrode. In a particular embodiment, the sensor(s) is (are) configured to detect roller movement, which may be indicative of a portion of a treatment protocol. The system may comprise one or more signaling devices such as a display, a light source, an acoustic source etc. for providing to an operator information and/or warning signals derived from the sensor signal(s). In case of an applicator having plural electrodes the sensor signal may be configured to provide signals, e.g. for movement data, for one or more individual electrodes and/or treatment areas.

In an embodiment with a controller and at least one sensor, the sensor(s) may be at least one of couplable and coupled to the controller and the controller is configured to control operation of the radio-frequency source in dependency of one or more signals from the sensor(s). Thus, feedback and safety control are facilitated, e.g. for preventing application of too much or too little radio-frequency energy with respect to one or more reference values. This facilitates optimizing treatment effectiveness. E.g., a system may be provided providing pulsed radio-frequency energy doses with a pulse-to-pulse delay time dependent on the rolling speed of the roller, the pulses being triggered by the sensor signal(s). Also, the controller may ensure that radio-frequency energy is only applied to electrodes that are actually in direct mechanical contact with the skin, so as to prevent discharges. Various systems for detecting (sufficiently good) contact between an RF electrode and skin are known and may be suitably employed.

In an embodiment the roller is releasably coupled to the manipulator and/or the applicator is releasably coupled to the radio-frequency source and/or a power source. Thus, exchanging of rollers is facilitated, facilitating use of specific rollers for specific treatments and/or treatment areas. It also facilitates customization, maintenance and/or repair of (parts of) the applicator. Different rollers may have (portions with) different diameters and/or differently shaped and/or sized electrodes.

The applicator may be a handheld device. In a handheld embodiment administrating the RF energy and performing treatment are facilitated. The radio-frequency source and the applicator may be provided as a single integrated device, possibly also including a power source such as a (possibly rechargeable) battery. Such integrated system may also be provided as a handheld device.

In an embodiment a shield is at least partially surrounding the roller. A shield increases safety, e.g. by ensuring that there is no interaction between the RF electrodes and non-intended treatment areas. In an embodiment, the operating portion comprises a hand grip, and the shield is arranged between the grip and the roller separating them. At least a portion of the shield may be formed to conform to the roller shape. The shield may be physically protecting and/or electrically protecting, e.g. at least a portion of the shield may be transparent for observing electrode position, treatment direction, and/or treatment progress, but preventing physical contact to the roller. Also, at least one portion of the shield may be a radio-frequency shield preventing emission of the radio-frequency energy as noise on other systems. A shield portion may be transparent for visible radiation but opaque for RF radiation, e.g. comprising a transparent conductive layer and/or a conductive grid of appropriate mesh size.

The system may be configured to induce contraction of collagen of a portion of the skin tissue by heating the portion of the skin tissue to a temperature in a range of 60-70 degrees Celsius, e.g. by providing an appropriate sensor and controller. Such system is safe and user friendly.

In an aspect a roller and a kit of parts with plural exchangeable rollers are provided. In the kit, at least some of the rollers may differ from each other with respect to the size, shape, number, arrangement and/or materials of the rollers and/or one or more of their electrodes. One or more rollers may also be provided as separate parts, e.g. for treatment of different body parts and/or replacement.

BRIEF DESCRIPTION OF THE DRAWINGS

The foregoing will be explained in more detail and with further benefits and aspects with reference to the appended drawings showing exemplary embodiments.

In the drawings.

DETAILED DESCRIPTION OF EMBODIMENTS

Figure 1:
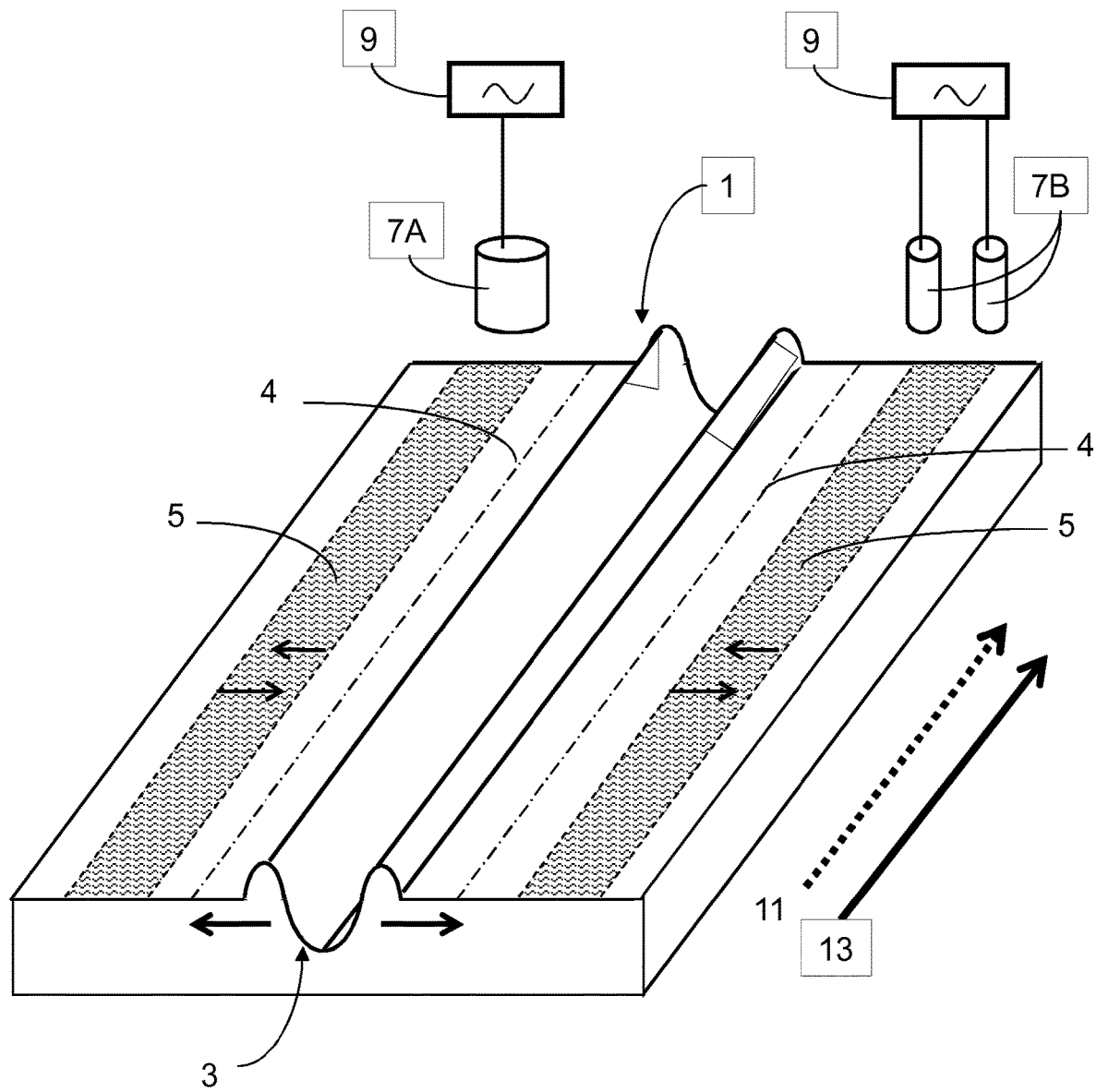
FIG. 1 indicates treatable skin tissue features for further reference.

It is noted that in the drawings, like features may be identified with like reference signs, where useful with alphabetic suffixes. It is further noted that the drawings are schematic, not necessarily to scale and that details that are not required for understanding the present invention may have been omitted. Terms "upward", "downward", "below", "above", and the like relate to the embodiments as oriented in the drawings.

FIG. 1 indicates a portion of skin 1, comprising a one dimensional skin relief feature 3, e.g. an elongated narrow wrinkle for at least part of which a portion of a perimeter 4 may be determined, e.g. by judging a deviation from the relief (e.g. the evenness) of adjacent skin tissue, e.g. surrounding skin. The feature and/or the perimeter need not be, and generally will not be, straight, symmetrical and/or at constant separation as indicated in FIG. 1. On each side of the relief feature 3 in a skin tissue area 5 contraction of the skin tissue is induced in a direction substantially orthogonal to (the local portion of the perimeter of) the feature 3 and parallel to the skin surface (indicated with narrow arrows). As a result, the skin tissue in between the contracted areas is pulled apart (indicated with bold arrows) and the feature 3 will be flattened. Thus, wrinkles and fine lines may be removed from the skin.

Similarly, differently shaped relief features may be flattened by suitably arranging the skin tissue areas and the direction of the contraction therein relative to the relief feature, e.g. radial forces may smoothen a generally rounded skin relief feature such as ice pick acne scars.

The skin tissue contraction is advantageously caused by collagen contraction which may be achieved by thermal activation, in particular heating, the skin. Human collagen may deform and contract when heated to a temperature in a range of about 60-70 degrees Celsius, so that heating to such temperatures is preferred. However, heating to higher temperatures and/or otherwise causing localized damage and/or small lesions in the skin tissue, e.g. by ablation of skin portions which may be intentionally caused by small RF arcs striking the skin, may also cause contraction of the skin tissue as a consequence of processes for healing and skin rejuvenation.

Suitably, the skin tissue is heated by RF energy by applying the RF energy to the skin tissue areas 5 on several positions along the relief feature by contacting the skin 1 with one or more radio-frequency electrodes. RF energy may be applied in a monopolar configuration with a single electrode 7A connected to an RF source 9 contacting the skin in the treatment area 5 and a second electrode (not shown) connected to the skin at a remote location. Preferred is, however, bipolar RF field generation between two adjacent electrodes 7B contacting the skin, more preferably with the bipolar electrodes arranged adjacent to each other substantially in a direction substantially perpendicular to the local direction of extension of the perimeter of the relief feature.

Inducing contraction along the relief feature is efficiently achieved by displacing the RF electrode(s) 7A, 7B along the relief feature 3 and contacting the skin intermittently, in a plurality of positions to provide a plurality of separate contact areas, as indicated with the bold broken arrow 11 or, preferred, with the electrode(s) in constant contact with the skin or placed in a series of partly overlapping contact areas to provide a continuous contracted skin tissue area, as indicated with the continuous arrow 13. For effective treatment, opposite sides of a relief feature may be treated simultaneously or subsequently.

Causing significant heating may also trigger skin tissue regeneration, amplifying and prolonging the rejuvenation effect.

Figure 2:
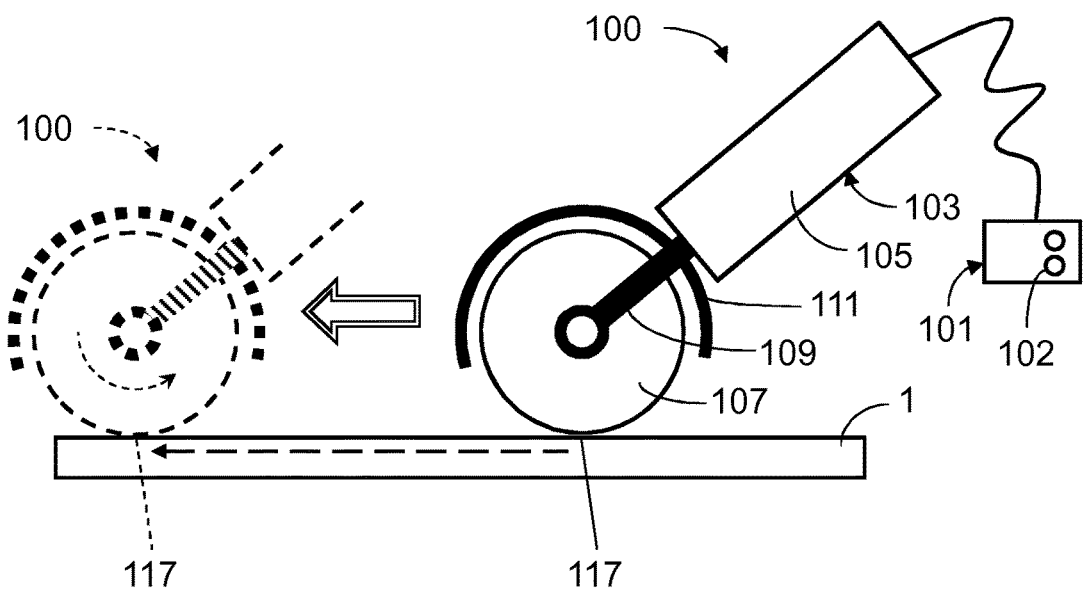
FIG. 2 is a side view an embodiment of a disclosed system for treating skin tissue.
Figure 3:
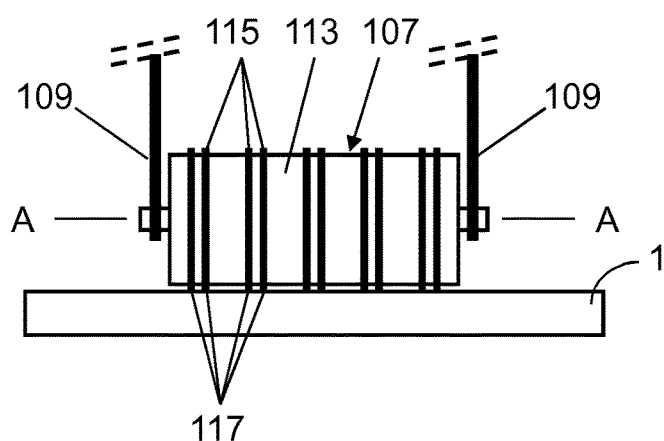
FIG. 3 is a partial front view of the embodiment of FIG. 2.

FIGS. 2 and 3 elucidate realizing the presently provided system and method. FIG. 2 indicates a system 100 for treating skin 1 with electromagnetic energy. The system 100 comprises a radio-frequency source 101 with an optional user interface 102 and a handheld applicator 103, which comprises a manipulator 105 and a roller 107, coupled to the manipulator 105. Here, the coupling comprises a fork 109. The applicator 103 comprises an optional shield 111 partially surrounding the roller 107. Optionally, the applicator comprises a user interface. A user interface may comprise one or more push buttons, dials, signaling lights, displays etc. (not shown). In an embodiment (not shown) a radio-frequency source 101 and/or an associated power source may be integrated in the applicator.

FIG. 3 shows a portion of the skin 1, the roller 107 and part of the fork 109, with the manipulator 105 and the shield 111 omitted for clarity. The roller 107 comprises an insulating body 113 rotatably arranged in the fork 109 about an axis of rotation A. A plurality of radio-frequency electrodes 115 contacting the skin 1 at respective contact areas (generally indicated with reference numeral 117) are arranged on the body 113. In FIG. 3, the electrodes 115 are substantially pair-wise parallel adjacent to each other and are offset in the axial direction with respect to the axis of rotation A, being arranged at a mutual distance in an axial direction of the axis of rotation. The electrodes 115 provide continuous and generally annular contact surfaces extending circumferentially about the axis of rotation A.

In operation, the electrodes 115 are placed on the skin 1 to be treated in contact with the skin surface, providing a row of contact areas 117 adjacent to each other generally along the axis of rotation A. One or more RF signals are applied to the electrodes 115 (see also below) which cause deposition of RF energy into the skin 1 at the contact area 117 resulting in heating of the skin tissue. By displacing the applicator as indicated in FIG. 2 by the bold arrow and dotted lines, the roller 107 with the electrodes 115 is rolled over the skin 1 in constant contact with the skin 1 and successive overlapping contact areas 117 are provided over the skin 1, so that a portion of the treatment area may be substantially continuously treated. Since contact between the electrodes 117 and the skin 1 is maintained during the displacement, treatment position and effectiveness can be reliably maintained and potentially harmful discharges are prevented.

The electrodes 115 on the roller 107 allow creation of continuous parallel lines of thermally induced tissue contraction in the dermis. The direction and length of the contraction lines are easily controllable by appropriately manipulating the applicator. By directing the contraction of the collagen orthogonal to the orientation of anatomic tension lines, wrinkles and/or fine lines can be flattened, cf. FIG. 1.

Figures 4A, 4B, 4C:
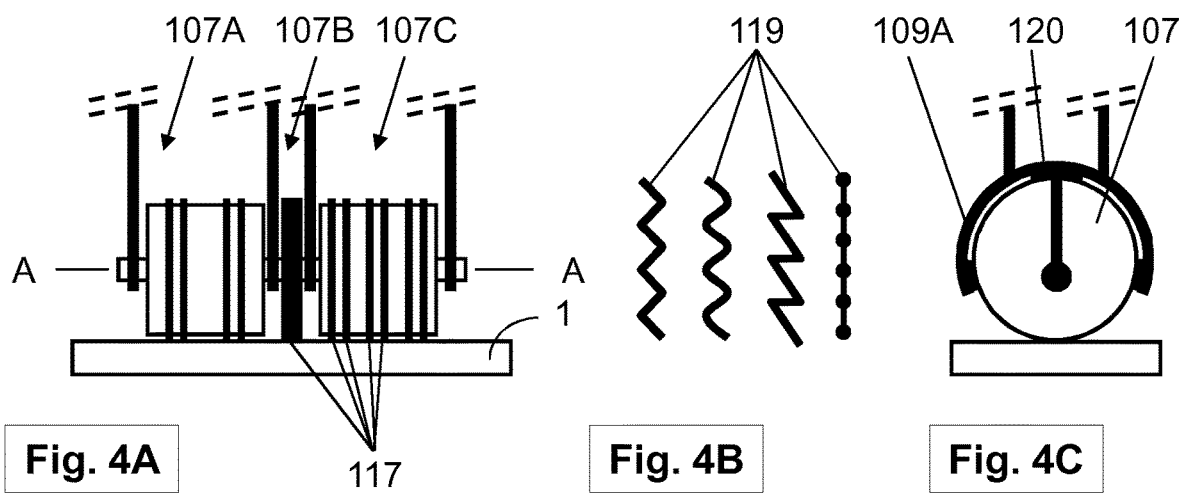
FIG. 4A-4C indicate (details of) different embodiments.

FIG. 4A shows, similar to FIG. 3, a different embodiment, comprising plural rollers 107A-C arranged adjacent to each other but having a common axis of rotation A. The different rollers 107A-C have different electrode arrangements, with roller 107B providing a single electrode contact surface, e.g.

for mono-polar RF treatment. In the applicator, electrodes 115 of each roller 107A-C may be operated and controlled individually and/or in groups, possibly with different radio frequencies and/or from different RF sources, and/or each roller 107A-C may be individually removed and/or exchanged.

FIG. 4B indicates different shapes of electrode contact surfaces 119 which may be used on a roller: zigzagging, undulating, saw-toothed and/or having a spatially varying width.

FIG. 4C indicates an embodiment wherein the roller 107 is a generally spherical ball with a conductive surface, held in a suitable coupling for coupling to a manipulator with appropriate degree of rotational freedom. Here, the coupling comprises a clamping claw 109A with an RF conducting contact 120 which allows the roller to rotate freely in the coupling. Different couplings may also be provided. A manipulator may comprise plural ball shaped electrodes, adjacent each other and/or arranged in an array.

Figure 5:
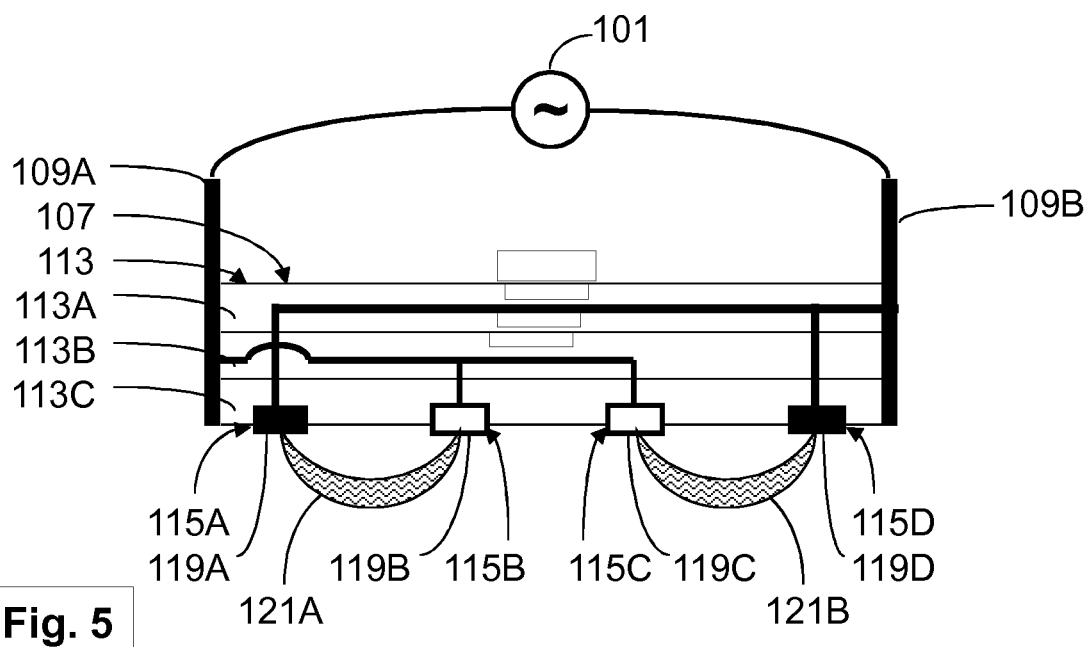
FIG. 5 indicates a portion of an electric circuit for use in the disclosed system.
Figure 6A:
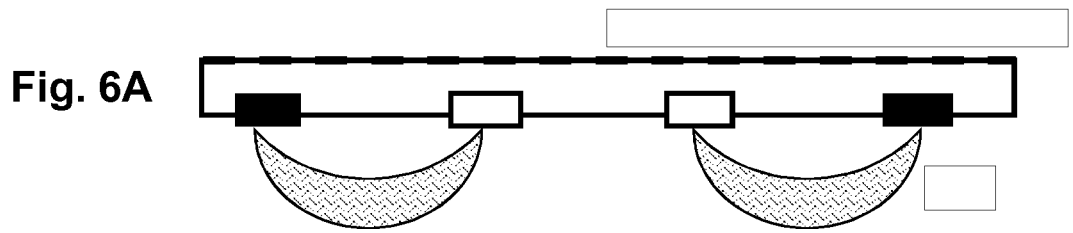
FIGS. 6A-D show details of embodiments of electrode geometries and operating modes for embodiments of the disclosed system.
Figure 6B:
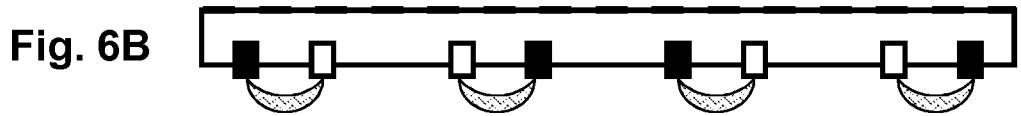
Figure 6C:
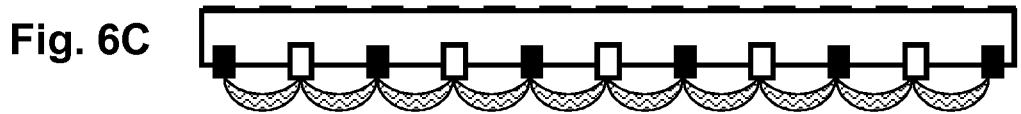
Figure 6D:
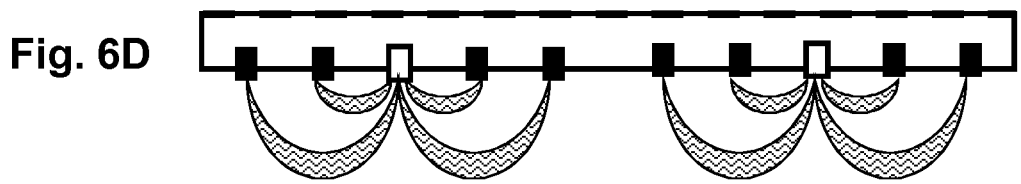

FIG. 5 schematically shows a portion roller 107 and legs 109A-B of an associated applicator fork of an exemplary embodiment. The roller 107 comprises a body 113 and RF electrodes 115A-D which are arranged on the roller 113 providing outward accessible contact surfaces 119A-D for contacting the treated skin. The RF electrodes 115A, 115D and 115B-C, respectively, are electrically connected to opposite poles of the RF source 101. In this example, the roller 103 has several insulating layers 113A-C, and the connections of the electrodes 115A, 115D and 115B-C are routed through different layers 113A-C and different legs 109A-B of the applicator, but other arrangements may be provided. The connections of the electrodes 115A-D facilitate bipolar operation to provide adjacent RF fields 121A-B extending between the electrodes 115A-B and 115C-D, respectively, for heating skin tissue in contact with the electrodes 115A-D.

For treatment of a one-dimensional skin relief feature 3 (see FIG. 1), the electrodes 115B, 115C may be arranged on opposite sides of the relief feature, so that skin tissue areas 5 adjacent the feature 3 are contacted by a pair of electrodes 115A and 115B on one side and a pair of electrodes 115C and 115D on the opposite side for simultaneous RF treatment of the feature 3. Rolling the roller over and along the feature in its longitudinal direction ensures contemporaneous displacement of the electrodes on opposite sides of and parallel to the skin tissue relief feature and treatment of the feature along its length (cf. FIG. 1).

FIGS. 6A-D show different configurations of electrode (operation), and the resulting RF fields, and further configurations will be apparent to the skilled person from contemplating the present disclosure. It is noted that different separation of electrodes may result in different treatment depths, e.g. due to different distributions of the RF energy within the skin tissue.

Figure 7:
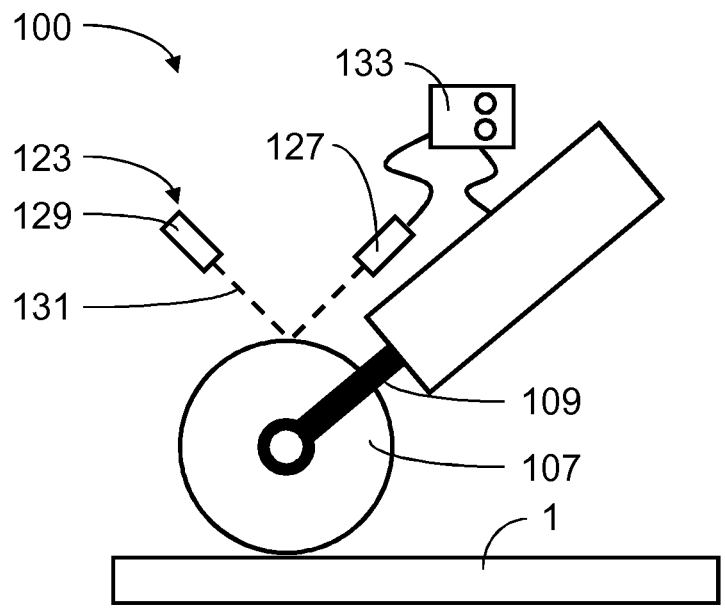
FIGS. 7-8 indicate sensor arrangements for the disclosed system.
Figure 8:
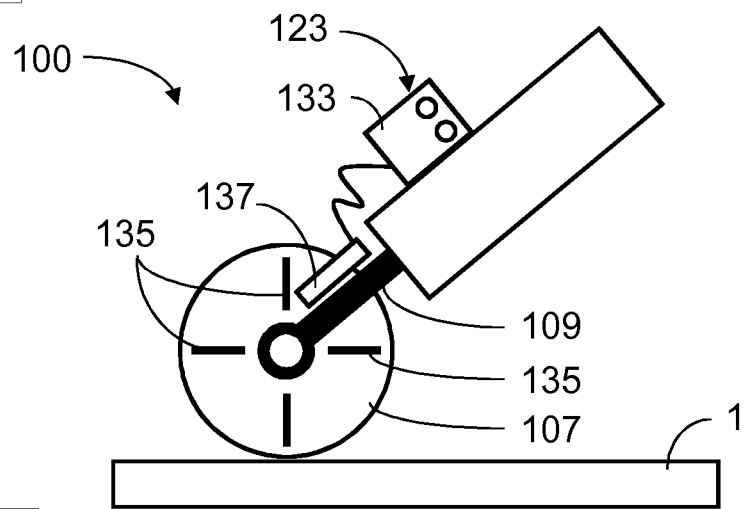

FIG. 7 illustrates an embodiment of a displacement sensor, here a roller movement sensor 123. The sensor 123 comprises an optical sensor, having an optical detector 127 for observing a portion of the roller 107 and detecting variations in the observed illumination pattern. A light source 129 is provided for illuminating the portion of the roller 107 observed by the detector 127 to improve detection reliability, e.g. with a light beam 131. The detector 127 may comprise a photodiode and/or a camera, e.g. as in a computer mouse, and the roller 107 may comprise optical markings, e.g. a distinct pattern that may be repetitive such as reflective stripes at constant separation along the roller circumference. Signals from the detector 127 may be provided to a controller 133 of the system 100 and/or to a user interface, which may be part of the controller 133. Different sensors such as mechanical, conductive, capacitive, etc may be provided. E.g., FIG. 8 illustrates an embodiment of a roller movement sensor 123 wherein the roller 107 comprises magnetic portions 135 and an inductive detector 137 for detecting movement of a magnetic portion 135 past it.

In another embodiment (not shown), the roller 107 is provided with detection electrodes on predetermined positions along its circumference, and the sensor is configured to detect electrical contact between the detection electrodes and the skin, e.g. by the skin short circuiting adjacent electrodes and/or changing capacitance of a detection electrode.

Figure 9:
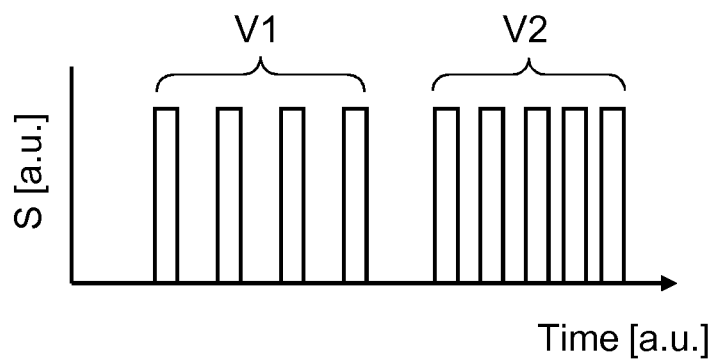
FIG. 9 indicates possible sensor data indicative of roller movement.

Rotation of the roller 107 is detected by the sensor 127, 137. Different rollers and/or electrode configurations may be associated with distinct markings and/or detection patterns, e.g. reflective stripe patterns. The controller 133 and/or sensor 127, 137 may be programmable with information relating to the roller(s) present in the applicator, e.g. to detect and process the sensor signals in a predetermined way. Possibly, a roller and the applicator comprise cooperating structures for automatically programming the controller, e.g. a bar code and/or an electromagnetic code imprinted on the roller. An embodiment, e.g. FIG. 8 may provide pulsed signals to the controller 133, wherein different rolling speeds result in different pulse intervals and/or durations. E.g., FIG. 9 indicates a pulse sequence of signals S (arbitrary units) versus time (arbitrary units) obtained by first rolling a roller 103 with a first speed V1 and next rolling the roller at a second, higher speed V2. The pulses may be used as a trigger pulse for operation of the RF source 101.

In another embodiment, not shown, displacement of the applicator and/or of the electrode may also be measured with direct reference to the skin itself, e.g. with a camera-based optical sensor like a computer mouse sensor.

By detection of the displacement speed, in particular the roller speed, the RF energy dose applied via the electrodes 115 can be controlled. E.g., every (trigger) pulse may lead to a dose of RF energy to the skin, which may comprise a predetermined amount of RF energy within a predetermined amount of time. The dose can be (pre)determined based on the contact area of the electrode(s) on the skin and the dose needed to heat up the skin. Pulsed dosing can prevent overtreatment. A warning signal could be provided to indicate and/or prevent too fast displacement of the applicator (dosage time is longer than triggering time resulting in undertreatment) or too slow (cooling down of skin between two dosages, also resulting in undertreatment), e.g. a visual and/or an acoustic signal, possibly a tangible signal on the manipulator. Another possible embodiment involves a more complex system with a feedback loop, wherein the measured roller speed is used to dynamically adjust the RF dosage energy.

Figure 10A:
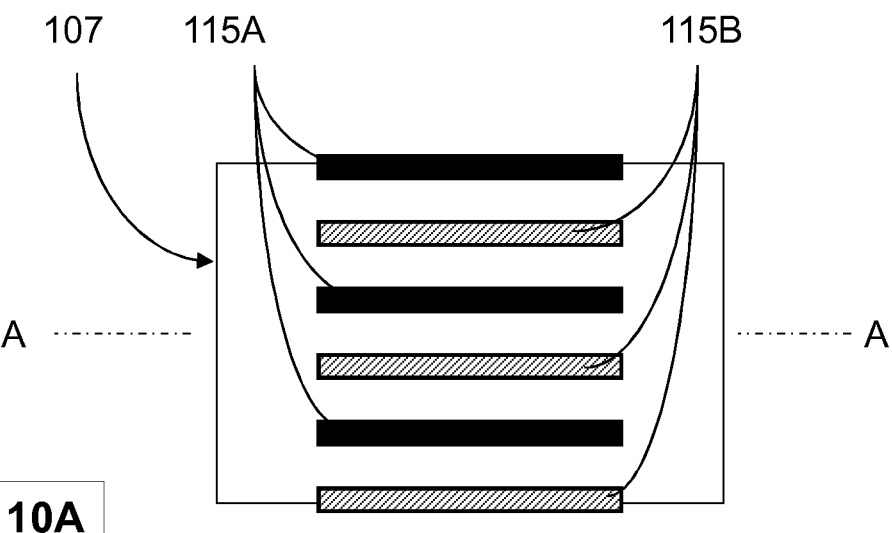
FIGS. 10A-10C show different electrode geometries.
Figure 10B:
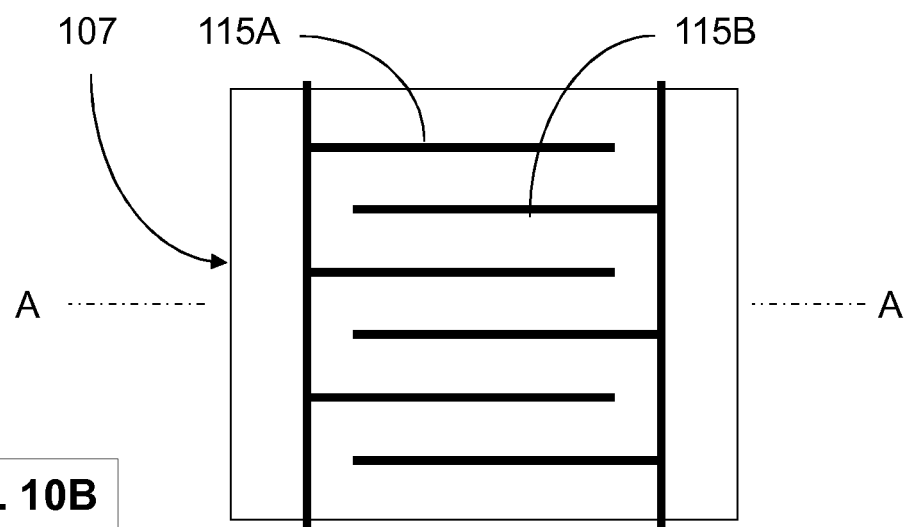
Figure 10C:
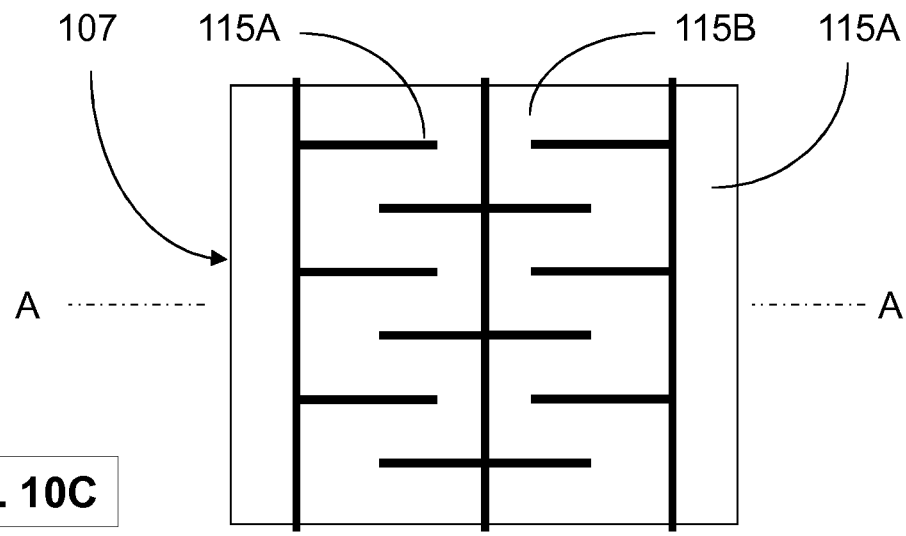

FIGS. 10A-10C show different electrode geometries, particularly suited for use with bipolar RF fields. In FIG. 10A electrodes 115A, 115B comprise contact surfaces which are arranged in axial direction A of a roller 107 connected alternatively to the RF source (not shown) for bipolar operation. A sensor and a controller monitor contact between each successive pair of electrodes 115A, 115B and the skin, so as to apply the RF energy between the electrodes 115A, 115B in contact with the skin surface and prevent unwanted discharges. When rolling the roller of FIG. 10A over the skin a series of successive contact areas that are treated with RF energy between successive pairs of electrodes 115A, 115B are provided. In this case of FIG. 10A the RF field direction will be primarily perpendicular to the axis A. Such arrangement may in particular be used with rollers having a non-circular, e.g. faceted, rolling surface. The separation between the treatment areas may be well known with such embodiment. Axially and/or circumferentially staggered electrodes may also be provided.

FIGS. 10B, 10C show electrode structures having perpendicular sections wherein the contact surfaces have interleaving fingers parallel to the axis A and a substantially circumferential connecting portion perpendicular to the axis A. Such arrangements may provide undulating directions of the RF field, with associated contraction directions. This may help providing a natural looking, non-uniformly tightened skin, e.g. for large skin surfaces having striae. Further, the arrangements of FIGS. 10B-10C may ensure constant contact between the skin and the electrodes, which may prevent discharges without requiring a sensor and controller.

Further embodiments may be provided, e.g. the shield may be larger or smaller, the rollers may be larger or smaller in any direction. A roller may be entirely conductive, etc. Further systems may be provided, e.g. a system for heating (at least a portion of) the roller, and/or an illumination system.

The disclosed embodiments may be suitable for domestic use, use in beauty salons and for medical use, possibly dependent on RF frequencies, RF powers, and/or aesthetic and hygienic considerations.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A system for treating skin tissue with radio-frequency energy, comprising:
   a radio-frequency source,
   an applicator comprising a manipulator, a fork and multiple rollers rotatable about a common axis of rotation,
   wherein each of said multiple rollers comprise an insulating body rotatably arranged in the fork about said common axis of rotation and at least one radio-frequency electrode is arranged on the insulating body of said each of said multiple rollers for contacting a skin surface of the skin tissue to be treated at successive contact areas of the skin surface,
   wherein at least a first roller from among of said multiple rollers provides a single radio-frequency electrode contact surface for mono-polar RF treatment,
   wherein the at least one radio-frequency electrode associated with said each of said multiple rollers provides a generally annular contact surface extending circumferentially about the common axis of rotation,
   wherein at least a second roller from among said multiple rollers comprises two rows of generally annular parallel contact surfaces on said insulating body and adjacent to each other offset in an axial direction with respect to the common axis of rotation to allow creation of continuous parallel lines of thermally induced tissue contraction in a dermis region of the skin tissue to be treated,
   wherein at least a third roller from among of said multiple rollers comprises three rows of generally annular contact parallel contact surfaces on said insulating body and adjacent to each other along the common axis of rotation to allow creation of continuous parallel lines of thermally induced tissue contraction in said dermis region of the skin tissue to be treated,
   wherein the at least one radio-frequency electrode is arranged at a mutual distance in the axial direction of the common axis of rotation for contacting the skin surface of the skin tissue to be treated concurrently at respective contact areas,
   wherein the at least one radio-frequency electrode is couplable or coupled with the radio-frequency source for applying radio-frequency energy to the skin tissue to be treated,
   wherein the system is configured to apply the radio-frequency energy to the skin tissue only via direct mechanical contact between the at least one radio-frequency electrode and the skin surface of the skin tissue to be treated when said each of said multiple rollers are in direct mechanical contact with the skin surface,
   wherein said each of said multiple rollers are rotatable about the common axis of rotation over a first angular range, and
   wherein the at least one radio-frequency electrode has a contact surface for contacting the skin surface of the skin tissue to be treated continuously extending about the common axis of rotation over a second angular range equal to or larger than the first angular range.

2. The system according to claim 1, wherein the at least one radio-frequency electrode comprises at least two pairs of bipolar radio-frequency electrodes arranged at a mutual distance in the axial direction and rotatable about the common axis of rotation and couplable or coupled with the radio-frequency source for bipolar operation.

3. The system according to claim 1, comprising at least one sensor configured to provide a signal indicative of at least one of: i) contact between the radio-frequency electrode and the skin tissue to be treated, or ii) radio-frequency power deposition into the skin tissue to be treated, or iii) treatment effectiveness or iv) roller movement with respect to at least one of an applicator portion and the skin surface of the skin tissue to be treated.

4. The system according to claim 3, wherein the system comprises a controller for controlling operation of the radio-frequency source and wherein the sensor is at least one of couplable and coupled to the controller and the controller is configured to control operation of the radio-frequency source in dependency of one or more signals from the sensor.

5. The system according to claim 1, wherein the system is configured to induce contraction of collagen of a portion of the skin tissue to be treated by heating the portion of the skin tissue to be treated to a temperature in a range of 60-70 degrees Celsius.

6. The system according to claim 1, further comprising a feedback system to maintain a portion of a skin temperature in a range of 60-70 degrees Celsius for a period of time, wherein the system is configured to induce contraction of collagen of a portion of the skin tissue to be treated by heating the portion of the skin tissue to be treated to a temperature in the range of 60-70 degrees Celsius which is controlled by monitoring the skin tissue temperature via said feedback system.

7. The system according to claim 1, wherein in one mode of operation wherein the rollers are operated individually, said multiple rollers are operated with different radio frequencies and/or different RF sources.

8. The system according to claim 1, wherein said each of the multiple rollers may be individually removed or replaced.

9. The system according to claim 1, wherein a feedback system maintains a portion of a skin temperature at a desired temperature for a desired period of time.

10. The system according to claim 1, wherein the at least one radio-frequency electrode associated with said each of said multiple rollers can be operated and controlled either individually or in groups or both individually and in groups.

11. The system according to claim 1, wherein the multiple rollers have different electrode arrangements.

12. The system according to claim 1, wherein said multiple rollers may be operated and controlled with different radio frequencies.

13. The system according to claim 1, wherein said multiple rollers may be operated and controlled from different RF sources.

14. A roller for preferred use in an applicator, said applicator comprising a manipulator, a fork and said roller, said roller comprising:
- at least two rows of annular radio-frequency electrodes arranged on an insulating body configured for contacting a skin surface of the skin tissue to be treated at successive contact areas of the skin surface of the skin tissue to be treated and for applying radio-frequency energy to the skin tissue to be treated,
- wherein the at least two rows of annular radio-frequency electrodes provide a generally annular contact surface extending circumferentially about a common axis of rotation,
- wherein the at least two rows of annular radio-frequency electrodes are configured as at least two rows of annular contact surfaces adjacent to each other along the common axis of rotation to allow creation of continuous parallel lines of thermally induced tissue contraction in a dermis region of the skin tissue to be treated,
- wherein the at least two rows of annular radio-frequency electrodes are arranged on the insulating body as being pair-wise parallel adjacent to each other and offset in the axial direction with respect to the common axis of rotation,
- wherein the at least two rows of annular radio-frequency electrodes are arranged on the insulating body at a mutual distance in the axial direction of the common axis of rotation,
- wherein the at least two rows of annular radio-frequency electrodes are couplable to a radio-frequency source, and
- wherein the roller is configured to be rotationally coupled to the manipulator for rotation with respect to the common axis of rotation causing the at least two rows of radio-frequency electrodes to contact the successive contact areas of the skin surface of the skin tissue to be treated by rotation of the roller over the skin surface of the skin tissue to be treated, and
- wherein the roller is configured to apply the radio-frequency energy to the skin tissue to be treated only via direct mechanical contact of the at least two rows of annular radio-frequency electrodes with the skin surface to be treated when the roller is in direct mechanical contact with the skin surface to be treated,
- wherein the roller is rotatable about the common axis of rotation over a first angular range and wherein each of the at least two rows of annular radio-frequency electrodes have a non-interrupted continuous circular contact surface for contacting the skin surface to be treated continuously extending about the common axis of rotation over a second angular range equal to or larger than the first angular range.

15. A system for treating skin tissue with radio-frequency energy, comprising:
- a radio-frequency source,
- a power source,
- a user interface,
- an applicator comprising a manipulator, a fork and a roller coupled to the manipulator rotatable about a common axis of rotation,
- a shield partially surrounding the roller,
- wherein the radio-frequency source and the power source are integrated into the applicator,
- wherein the roller comprises an insulating body rotatably arranged in the fork about said common axis of rotation and a plurality of radio-frequency electrodes arranged on the insulating body of the roller arranged on the insulating body to contact a skin surface of the skin tissue to be treated at successive contact areas of the skin surface,
- wherein the plurality of radio-frequency electrodes are arranged at a mutual distance in an axial direction of the axis of rotation,
- wherein each of the plurality of radio-frequency electrodes each provide a continuous and generally annular contact surface circumferentially about the common axis of rotation,
- wherein said each of the plurality of radio-frequency electrodes provides a generally annular contact surface extending circumferentially about an entire common axis of rotation,
- wherein said each of the plurality of radio-frequency electrodes are couplable or coupled with the radio-frequency source for applying radio-frequency energy to the skin tissue to be treated,
- wherein the system is configured to apply the radio-frequency energy to the skin tissue to be treated only via direct mechanical contact between said each of the plurality of radio-frequency electrodes and the skin surface when the roller is in direct mechanical contact with the skin surface,
- wherein the roller is rotatable about the common axis of rotation over a first angular range, and
- wherein the at least one of said plurality of radio-frequency electrodes has a contact surface for contacting the skin surface continuously extending about the common axis of rotation about a second angular range equal to or larger than the first angular range.

* * * * *